(12) United States Patent
Betts et al.

(10) Patent No.: US 9,410,173 B2
(45) Date of Patent: Aug. 9, 2016

(54) TEMPLATE SWITCH-BASED METHODS FOR PRODUCING A PRODUCT NUCLEIC ACID

(71) Applicant: Clontech Laboratories, Inc., Mountain View, CA (US)

(72) Inventors: Craig Betts, Mountain View, CA (US); Andrew Alan Farmer, Mountain View, CA (US)

(73) Assignee: Clontech Laboratories, Inc., Mountain View, CA (US)

( * ) Notice: Subject to any disclaimer, the term of this patent is extended or adjusted under 35 U.S.C. 154(b) by 0 days.

(21) Appl. No.: 14/058,038

(22) Filed: Oct. 18, 2013

(65) Prior Publication Data

US 2014/0113332 A1  Apr. 24, 2014

Related U.S. Application Data

(60) Provisional application No. 61/717,973, filed on Oct. 24, 2012.

(51) Int. Cl.
*C12P 19/34* (2006.01)
*C12N 15/10* (2006.01)

(52) U.S. Cl.
CPC ............. *C12P 19/34* (2013.01); *C12N 15/1096* (2013.01); *C12Q 2521/107* (2013.01); *C12Q 2525/191* (2013.01)

(58) Field of Classification Search
CPC ............... C12Q 1/6806; C12Q 1/6853; C12Q 2521/107; C12Q 2525/155; C12Q 2525/161; C12Q 2525/173; C12Q 2525/191
See application file for complete search history.

(56) References Cited

U.S. PATENT DOCUMENTS

| | | | |
|---|---|---|---|
| 5,962,271 A | 10/1999 | Chenchik et al. | |
| 5,962,272 A | 10/1999 | Chenchik et al. | |
| 6,251,639 B1 * | 6/2001 | Kurn | C12Q 1/6844 435/6.1 |
| 6,406,890 B1 | 6/2002 | Mueller | |
| 2006/0099589 A1 | 5/2006 | Pedersen et al. | |
| 2008/0145844 A1 | 6/2008 | Barsova et al. | |
| 2012/0283106 A1 | 11/2012 | Wang et al. | |

FOREIGN PATENT DOCUMENTS

| | | |
|---|---|---|
| DE | 196 01 385 A1 | 7/1997 |
| EP | 1 369 480 A1 | 12/2003 |
| KR | 2002-0036665 A | 5/2002 |
| WO | 97/24455 A2 | 1/1996 |
| WO | WO 01/09310 A1 | 2/2001 |
| WO | WO 02-00938 A2 | 1/2002 |
| WO | 02/68629 A2 | 9/2002 |
| WO | WO 2005/019452 A1 | 3/2005 |
| WO | 2012/042374 A2 | 4/2012 |
| WO | WO 2012/116146 A1 | 8/2012 |
| WO | 2014/066179 A1 | 5/2014 |
| WO | WO 2015/173402 A1 | 11/2015 |

OTHER PUBLICATIONS

Kapteyn et al. BMC Genomics, 2010, 11: 413.*
Kurzynska-Kokorniak, et al. "DNA-directed DNA Polymerase and Strand Displacement Activity of the Reverse Transcriptase Encoded by the R2 Retrotransposon," Journal of Molecular Biology, vol. 374, No. 2, pp. 322-333 (2007).
Oz-Gleenberg et al., "Reverse transcriptases can clamp together nucleic acids strands with two complementary bases at their 3'-termini for initiating DNA synthesis," Nucleic Acids Research, vol. 39, No. 3, pp. 1042-1053, (2011).
Oz-Gleenberg et al., "Substrate variations that affect the nucleic acid clamp activity of reverse transcriptases," FEBS Journal, vol. 279, No. 10, pp. 1894-1903 (2012).
Islam et al. "Highly multiplexed and strand-specific single-cell RNA 5' end sequencing", Nature Protocols 7 (2012), 813-828.
Kivioja et al. "Counting absolute numbers of molecules using unique molecular identifiers", Nature Methods 9 (2012), 72-74.
Levin et al. "Comprehensive comparative analysis of strand-specific RNA sequencing methods", Nature Methods 7 (2010), 709-715.
Matz et al. "Amplification of cDNA ends based on template-switching effect and step-out PCR," Nucleic Acids Research, 1999, vol. 27, No. 6, 1558-1560.
Zhuang et al. "Structural bias in T4 RNA ligase-mediated 3'-adapter ligation", Nucleic Acids Research 40(7): e54 (2012), 14 pages.
Schramm et al. "A simple and reliable 5'-RACE approach", Nucleic Acids Research, 2000, vol. 28, No. 22, e96, 4 pages.
Turchinovich et al. "Capture and Amplification by Tailing and Switching (CATS): An ultrasensitive ligation-independent method for generation of DNA libraries for deep sequencing from pictogram amounts of DNA and RNA", RNA Biology, vol. 11, No. 7, pp. 817-828 (Jul. 2014).

* cited by examiner

*Primary Examiner* — Angela M Bertagna
(74) *Attorney, Agent, or Firm* — Bret E. Field; Bozicevic, Field & Francis LLP

(57) ABSTRACT

Provided are methods of producing a product nucleic acid. The methods include combining a template deoxyribonucleic acid (DNA), a polymerase, a template switch oligonucleotide, and dNTPs into a reaction mixture. The components are combined into the reaction mixture under conditions sufficient to produce a product nucleic acid that includes the template DNA and the template switch oligonucleotide each hybridized to adjacent regions of a single product nucleic acid that includes a region polymerized from the dNTPs by the polymerase. Aspects of the invention further include compositions and kits.

15 Claims, 1 Drawing Sheet

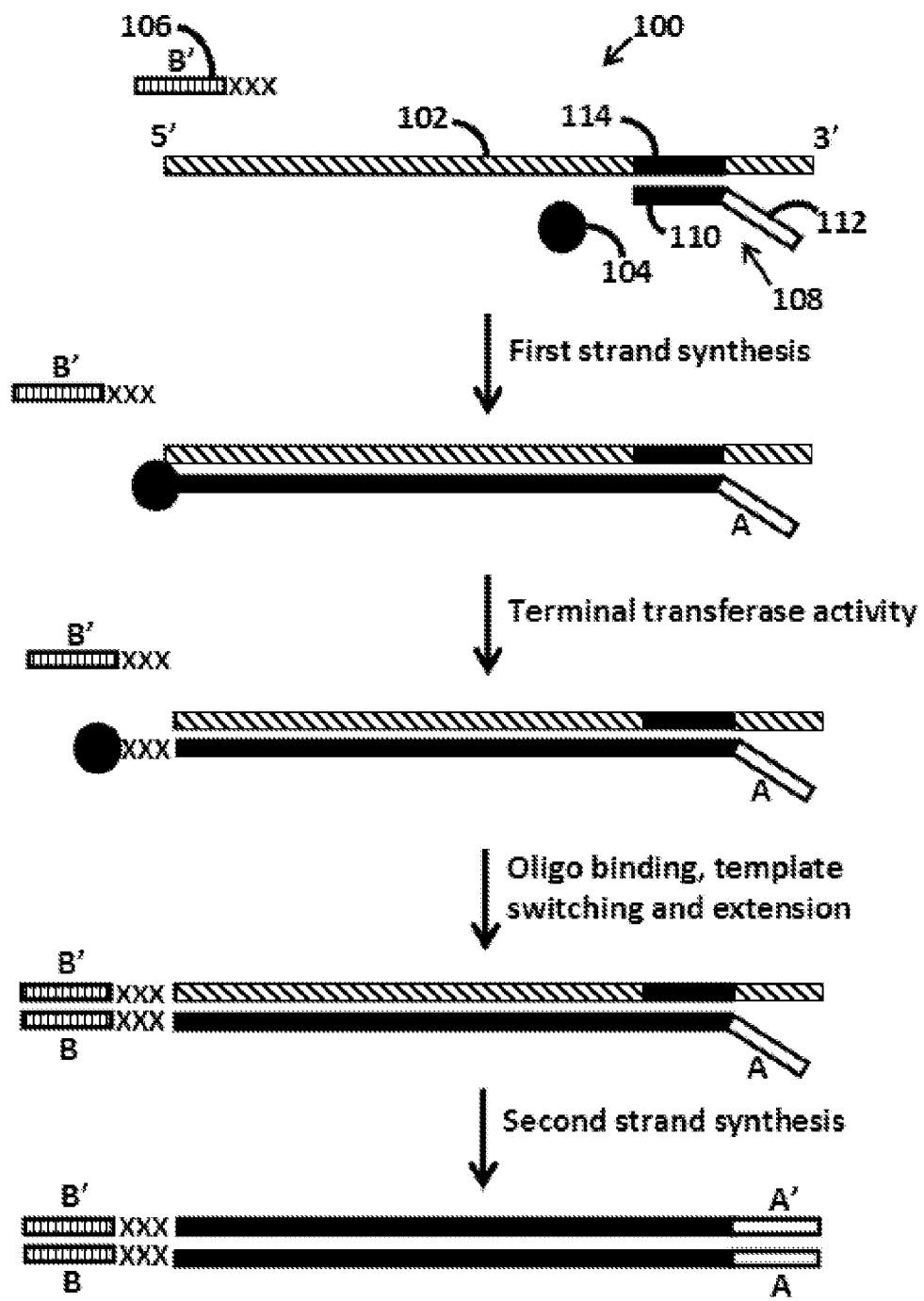

TEMPLATE SWITCH-BASED METHODS FOR PRODUCING A PRODUCT NUCLEIC ACID

INTRODUCTION

Methods of nucleic acid manipulation, such as polymerase chain reaction (PCR) and sequencing, typically require regions of known sequence. However, it is often the case that the identity and sequences of nucleic acids in a sample of interest is unknown. Methods have been developed to overcome this obstacle, such as the covalent addition of regions of known sequence to nucleic acids in the sample. In addition, researchers may wish to fuse DNA molecules, such as cloning nucleic acids of interest into vectors. Common methods include covalent ligation of DNA molecules using DNA or RNA ligases. The ligation reactions can be performed with or without regions of micro-homology (e.g., "sticky ends").

Methods currently used to add regions of known sequence to nucleic acids in a sample include ligation-based methods, e.g., blunt end ligation, ligation to "sticky ends," "A-tailing" followed by ligation, single-stranded ligation with an RNA ligase, and the like. A second strategy is the addition of homopolymeric ends by a terminal transferase or other enzyme suitable for non-templated nucleotide addition. A third common strategy is random or pseudo-random amplification using primers that have a defined 5' sequence and random or pseudo-random 3' terminus. Recombinase-based strategies for adding adapters to nucleic acids in a sample have also been employed.

A drawback of the above approaches is their lack of directionality, which makes it difficult to have different adapters at the different ends of the nucleic acids. A second drawback of these methods is sensitivity, where the methods are not suitable when only a small amount of sample is available.

SUMMARY

Provided are methods of producing a product nucleic acid. The methods include combining a template deoxyribonucleic acid (DNA), a polymerase, a template switch oligonucleotide, and dNTPs into a reaction mixture. The components are combined into the reaction mixture under conditions sufficient to produce a product nucleic acid that includes the template DNA and the template switch oligonucleotide each hybridized to adjacent regions of a single product nucleic acid that includes a region polymerized from the dNTPs by the polymerase. Aspects of the invention further include compositions and kits.

BRIEF DESCRIPTION OF THE FIGURES

FIG. 1 schematically illustrates a template switch-based method for producing a product nucleic acid according to one embodiment of the present disclosure.

DETAILED DESCRIPTION

Provided are methods of producing a product nucleic acid. The methods include combining a template deoxyribonucleic acid (DNA), a polymerase, a template switch oligonucleotide, and dNTPs into a reaction mixture. The components are combined into the reaction mixture under conditions sufficient to produce a product nucleic acid that includes the template DNA and the template switch oligonucleotide each hybridized to adjacent regions of a single product nucleic acid that includes a region polymerized from the dNTPs by the polymerase. Aspects of the invention further include compositions and kits.

Before the methods of the present disclosure are described in greater detail, it is to be understood that the methods are not limited to particular embodiments described, as such may, of course, vary. It is also to be understood that the terminology used herein is for the purpose of describing particular embodiments only, and is not intended to be limiting, since the scope of the methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. The upper and lower limits of these smaller ranges may independently be included in the smaller ranges and are also encompassed within the methods, subject to any specifically excluded limit in the stated range. Where the stated range includes one or both of the limits, ranges excluding either or both of those included limits are also included in the methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods belong. Although any methods similar or equivalent to those described herein can also be used in the practice or testing of the methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present methods are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, which are, for clarity, described in the context of separate embodiments, may also be provided in combination in a single embodiment. Conversely, various features of the methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order which is logically possible.

Methods

Methods of producing a product nucleic acid are provided. The methods utilize the ability of certain nucleic acid polymerases to "template switch," using a first nucleic acid strand as a template for polymerization, and then switching to a second template nucleic acid strand (which may be referred to as a "template switch nucleic acid" or an "acceptor template") while continuing the polymerization reaction. The result is the synthesis of a hybrid nucleic acid strand with a 5' region complementary to the first template nucleic acid strand and a 3' region complementary to the template switch nucleic acid. In certain aspects, the nucleotide sequence of all or a portion (e.g., a 5' region) of the template switch nucleic acid may be defined by a practitioner of the subject methods such that the newly-synthesized hybrid nucleic acid strand has a nucleotide sequence at its 3' end useful for a downstream application(s) of interest, e.g., PCR amplification, cloning, sequencing, and/or any other downstream application(s) of interest.

The subject methods include combining a template deoxyribonucleic acid (DNA), a polymerase, a template switch oligonucleotide, and dNTPs into a reaction mixture. The reaction mixture components are combined under conditions sufficient to produce a product nucleic acid that includes the template DNA and the template switch oligonucleotide each hybridized to adjacent regions of a single product nucleic acid that includes a region polymerized from the dNTPs by the polymerase.

By "conditions sufficient to produce a product nucleic acid" is meant reaction conditions that permit polymerase-mediated extension of a 3' end of a nucleic acid strand hybridized to the template DNA, template switching of the polymerase to the template switch oligonucleotide, and continuation of the extension reaction to the 5' end of the template switch oligonucleotide. Achieving suitable reaction conditions may include selecting reaction mixture components, concentrations thereof, and a reaction temperature to create an environment in which the polymerase is active and the relevant nucleic acids in the reaction interact (e.g., hybridize) with one another in the desired manner. For example, in addition to the template DNA, the polymerase, the template switch oligonucleotide and dNTPs, the reaction mixture may include buffer components that establish an appropriate pH, salt concentration (e.g., KCl concentration), metal cofactor concentration (e.g., $Mg^{2+}$ or $Mn^{2+}$ concentration), and the like, for the extension reaction and template switching to occur. Other components may be included, such as one or more nuclease inhibitors (e.g., an RNase inhibitor and/or a DNase inhibitor), one or more additives for facilitating amplification/replication of GC rich sequences (e.g., GC-Melt™ reagent (Clontech Laboratories, Inc. (Mountain View, Calif.)), betaine, DMSO, ethylene glycol, 1,2-propanediol, or combinations thereof), one or more molecular crowding agents (e.g., polyethylene glycol, or the like), one or more enzyme-stabilizing components (e.g., DTT present at a final concentration ranging from 1 to 10 mM (e.g., 5 mM)), and/or any other reaction mixture components useful for facilitating polymerase-mediated extension reactions and template-switching.

The reaction mixture can have a pH suitable for the primer extension reaction and template-switching. In certain embodiments, the pH of the reaction mixture ranges from 5 to 9, such as from 7 to 9, including from 8 to 9, e.g., 8 to 8.5. In some instances, the reaction mixture includes a pH adjusting agent. pH adjusting agents of interest include, but are not limited to, sodium hydroxide, hydrochloric acid, phosphoric acid buffer solution, citric acid buffer solution, and the like. For example, the pH of the reaction mixture can be adjusted to the desired range by adding an appropriate amount of the pH adjusting agent.

The temperature range suitable for production of the product nucleic acid may vary according to factors such as the particular polymerase employed, the melting temperatures of any optional primers employed, etc. According to one embodiment, the polymerase is a reverse transcriptase (e.g., an MMLV reverse transcriptase) and the reaction mixture conditions sufficient to produce the product nucleic acid include bringing the reaction mixture to a temperature ranging from 4° C. to 72° C., such as from 16° C. to 70° C., e.g., 37° C. to 50° C., such as 40° C. to 45° C., including 42° C.

The template deoxyribonucleic acid (DNA) may be a polymer of any length composed of deoxyribonucleotides, e.g., 10 bases or longer, 20 bases or longer, 50 bases or longer, 100 bases or longer, 500 bases or longer, 1000 bases or longer, 2000 bases or longer, 3000 bases or longer, 4000 bases or longer, 5000 bases or longer 10,000 bases or longer, 50,000 bases or longer or more bases. The template DNA may be a double-stranded DNA template (dsDNA template) or a single-stranded DNA template (ssDNA template).

The DNA sample that includes the template DNA may be combined into the reaction mixture in an amount sufficient for producing the product nucleic acid. According to one embodiment, the DNA sample is combined into the reaction mixture such that the final concentration of DNA in the reaction mixture is from 1 fg/µL to 10 µg/µL, such as from 1 pg/µL to 5 µg/µL, such as from 0.001 µg/µL to 2.5 µg/µL, such as from 0.005 µg/µL to 1 µg/µL, such as from 0.01 µg/µL to 0.5 µg/µL, including from 0.1 µg/µL to 0.25 µg/µL. In certain aspects, the DNA sample that includes the template DNA is isolated from a single cell. In other aspects, the DNA sample that includes the template DNA is isolated from 2, 3, 4, 5, 6, 7, 8, 9, 10, 20, 50, 100, 500 or more cells.

The template DNA may be present in any nucleic acid sample of interest, including but not limited to, a nucleic acid sample isolated from a single cell, a plurality of cells (e.g., cultured cells), a tissue, an organ, or an organism (e.g., bacteria, yeast, or the like). In certain aspects, the nucleic acid sample is isolated from a cell(s), tissue, organ, and/or the like of a mammal (e.g., a human, a rodent (e.g., a mouse), or any other mammal of interest). In other aspects, the nucleic acid sample is isolated from a source other than a mammal, such as bacteria, yeast, insects (e.g., drosophila), amphibians (e.g., frogs (e.g., *Xenopus*)), viruses, plants, or any other non-mammalian nucleic acid sample source.

The template DNA may be any type of DNA of interest to a practitioner of the subject methods, including but not limited to genomic DNA or fragments thereof, complementary DNA (or "cDNA", synthesized from any RNA or DNA of interest), recombinant DNA (e.g., plasmid DNA), or the like.

Approaches, reagents and kits for isolating DNA from such sources are known in the art. For example, kits for isolating genomic DNA from a source of interest—such as the Nucleo-Mag®, NucleoSpin®, and NucleoBond® genomic DNA isolation kits by Clontech Laboratories, Inc. (Mountain View, Calif.)—are commercially available. In certain aspects, the genomic DNA is isolated from a fixed biological sample, e.g., formalin-fixed, paraffin-embedded (FFPE) tissue. Genomic DNA from FFPE tissue may be isolated using commercially available kits—such as the NucleoSpin® FFPE DNA kits by Clontech Laboratories, Inc. (Mountain View, Calif.).

In certain aspects, the subject methods include producing the template DNA from a precursor DNA (e.g., a precursor double-stranded DNA (dsDNA) or precursor single-stranded DNA (ssDNA)). For example, when it is desirable to control the size of the template DNA that is combined into the reaction mixture, a DNA sample isolated from a source of interest may be subjected to shearing/fragmentation, e.g., to generate a template DNA that is shorter in length as compared to a precursor non-sheared DNA (e.g., genomic DNA) in the original sample. The template DNA may be generated by a shearing/fragmentation strategy including, but not limited to, passing the sample one or more times through a micropipette tip or fine-gauge needle, nebulizing the sample, sonicating the sample (e.g., using a focused-ultrasonicator by Covaris, Inc. (Woburn, Mass.)), bead-mediated shearing, enzymatic shearing (e.g., using one or more DNA-shearing e.g., restriction, enzymes), chemical based fragmentation, e.g., using divalent cations, fragmentation buffer (which may be used in combination with heat) or any other suitable approach for shearing/fragmenting a precursor DNA to generate a shorter template DNA. In certain aspects, the template DNA generated by shearing/fragmentation of a starting nucleic acid sample has a length of from 50 to 10,000 nucleotides, from 100 to 5000 nucleotides, from 150 to 2500 nucleotides, from 200 to 1000 nucleotides, e.g., from 250 to 500 nucleotides in length. According to certain embodiments, the template DNA generated by shearing/fragmentation of a starting nucleic acid sample has a length of from 10 to 20 nucleotides, from 20 to 30 nucleotides, from 30 to 40 nucleotides, from 40 to 50 nucleotides, from 50 to 60 nucleotides, from 60 to 70 nucleotides, from 70 to 80 nucleotides, from 80 to 90 nucleotides, from 90 to 100 nucleotides, from 100 to 150 nucleotides, from 150 to 200, from 200 to 250 nucleotides in length, or from 200 to 1000 nucleotides or even from 1000 to 10,000 nucleotides, for example, as appropriate for the sequencing platform chosen.

Additional strategies for producing the template DNA from a precursor DNA may be employed. For example, if a precursor dsDNA has an overhang at one or both of its ends, it may be desirable to process the precursor DNA to generate a template dsDNA having blunt ends. Approaches for generating dsDNA with blunt ends are known in the art. For example, the large (Klenow) fragment of DNA polymerase I may be used to fill in 5' overhangs, while T4 DNA polymerase may be used to trim 3' overhangs.

In other aspects, a precursor dsDNA may have blunt ends and it may be desirable to generate and employ a template DNA having an overhang (e.g., a 3' overhang) at one or both of its ends. By "overhang" is meant one or more unpaired nucleotides at an end of an otherwise double-stranded DNA molecule. These overhangs may be useful, e.g., to provide a template-primer substrate for the polymerase. That is, when the template DNA has an overhang at one of its ends, the strand that is longer at that end can serve as the DNA template, while the strand that is shorter at that end can effectively serve as a primer for initiating a nucleic acid polymerization reaction. Accordingly, the addition of a primer to the reaction mixture is not necessary when the template DNA has an overhang at one (or both) of its ends, as a first strand synthesis reaction can occur by virtue of the overhang providing a template-primer substrate for the polymerase.

Strategies for generating DNA having overhangs are known and may include contacting/digesting a precursor dsDNA (e.g., a genomic DNA, a cDNA, or the like) with a restriction endonuclease, thereby producing a template DNA having an overhang (or "sticky end") at one or both ends of the template DNA. Restriction endonucleases and the types of overhangs generated thereby are well characterized and can be selected by one practicing the subject methods to produce a template DNA having a desired type of overhang.

Alternatively, or additionally, a DNA "tailing" reaction may be performed to generate a template DNA having a desired overhang. According to one embodiment, the subject methods include contacting a precursor DNA with a terminal transferase in the presence of one or more types of dNTPs under conditions sufficient to produce the DNA template having the desired overhang. The rate of addition of dNTPs—and thus the length of the overhang—is a function of the ratio of 3" DNA ends to the dNTP concentration, and also which dNTP is used. The terminal transferase reaction is carried out at a temperature at which the terminal transferase is active, such as between 30° C. and 50° C., including 37° C. The dNTPs in the terminal transferase reaction may be present at a final concentration of from 0.01 mM to 1 mM (each, if more than one of the four types of dNTPs is used), such as from 0.05 mM to 0.5 mm, including 0.1 mM. The precursor DNA may be present in the terminal transferase reaction at a concentration of from 0.05 to 500 pmol, such as from 0.5 to 50 pmol, including 1 to 25 pmol, e.g., 5 pmol. A terminal transferase buffer solution and any other useful components (e.g., a metal cofactor such as Co, or the like) may also be included in the terminal transferase reaction. The terminal transferase reaction results in the addition of nucleotides at the 3' end of one or both strands of the precursor dsDNA to generate a template DNA having one or two 3' overhangs. The resulting template DNA may then be combined into the reaction mixture for generating the product nucleic acid according to the subject methods.

The methods of the present disclosure include combining a polymerase into the reaction mixture. A variety of polymerases may be employed when practicing the subject methods. The polymerase combined into the reaction mixture is capable of template switching, where the polymerase uses a first nucleic acid strand as a template for polymerization, and then switches to the 3' end of a second template nucleic acid strand to continue the same polymerization reaction. In certain aspects, the polymerase combined into the reaction mixture is a reverse transcriptase. Reverse transcriptases capable of template-switching that find use in practicing the subject methods include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants derivatives, or functional fragments thereof. For example, the reverse transcriptase may be a Moloney Murine Leukemia Virus reverse transcriptase (MMLV RT) or a Bombyx mori reverse transcriptase (e.g., Bombyx mori R2 non-LTR element reverse transcriptase). Polymerases capable of template switching that find use in practicing the subject methods are commercially available and include SMARTScribe™ reverse transcriptase available from Clontech Laboratories, Inc. (Mountain View, Calif.). In certain aspects, a mix of two or more different polymerases is added to the reaction mixture, e.g., for improved processivity, proof-reading, and/or the like.

The polymerase is combined into the reaction mixture such that the final concentration of the polymerase is sufficient to produce a desired amount of the product nucleic acid. In certain aspects, the polymerase (e.g., a reverse transcriptase such as an MMLV RT or a Bombyx mori RT) is present in the reaction mixture at a final concentration of from 0.1 to 200 units/µL (U/µL), such as from 0.5 to 100 U/µL, such as from 1 to 50 U/µL, including from 5 to 25 U/µL, e.g., 20 U/µL.

In addition to a template switching capability, the polymerase combined into the reaction mixture may include other useful functionalities to facilitate production of the product nucleic acid. For example, the polymerase may have terminal transferase activity, where the polymerase is capable of catalyzing the addition of deoxyribonucleotides to the 3' hydroxyl terminus of a DNA molecule. In certain aspects, when the polymerase reaches the 5' end of the template DNA, the polymerase is capable of incorporating one or more additional nucleotides at the 3' end of the nascent strand not encoded by the template. For example, when the polymerase has terminal transferase activity, the polymerase may be capable of incorporating 1, 2, 3, 4, 5, 6, 7, 8, 9, 10 or more additional nucleotides at the 3' end of the nascent DNA strand. All of the nucleotides may be the same (e.g., creating a homonucleotide stretch at the 3' end of the nascent strand) or at least one of the nucleotides may be different from the other(s). In certain aspects, the terminal transferase activity of the polymerase results in the addition of a homonucleotide stretch of 2, 3, 4, 5, 6, 7, 8, 9, 10 or more of the same nucleotides (e.g., all dCTP, all dGTP, all dATP, or all dTTP). For example, according to one embodiment, the polymerase is an MMLV reverse transcriptase (MMLV RT). MMLV RT incorporates additional nucleotides (predominantly dCTP, e.g., three dCTPs) at the 3' end of the nascent DNA strand. As described in greater detail elsewhere herein, these additional nucleotides may be useful for enabling hybridization between the 3' end of a template switch oligonucleotide and the 3' end of the nascent DNA strand, e.g., to facilitate template switching by the polymerase from the template DNA to the template switch oligonucleotide.

As set forth above, the subject methods include combining a template switch oligonucleotide into the reaction mixture. By "template switch oligonucleotide" is meant an oligonucleotide template to which a polymerase switches from an initial template (e.g., the template DNA in the subject methods) during a nucleic acid polymerization reaction. In this regard, the template DNA may be referred to as a "donor template" and the template switch oligonucleotide may be referred to as an "acceptor template." As used herein, an "oligonucleotide" is a single-stranded multimer of nucleotides from 2 to 500 nucleotides, e.g., 2 to 200 nucleotides. Oligonucleotides may be synthetic or may be made enzymatically, and, in some embodiments, are 10 to 50 nucleotides in length. Oligonucleotides may contain ribonucleotide monomers (i.e., may be oligoribonucleotides or "RNA oligonucleotides") or deoxyribonucleotide monomers (i.e., may be oligodeoxyribonucleotides or "DNA oligonucleotides"). Oligonucleotides may be 10 to 20, 21 to 30, 31 to 40, 41 to 50, 51-60, 61 to 70, 71 to 80, 80 to 100, 100 to 150 or 150 to 200, up to 500 or more nucleotides in length, for example.

The reaction mixture includes the template switch oligonucleotide at a concentration sufficient to readily permit template switching of the polymerase from the template DNA to the template switch oligonucleotide. For example, the template switch oligonucleotide may be added to the reaction mixture at a final concentration of from 0.01 to 100 µM, such as from 0.1 to 10 µM, such as from 0.5 to 5 µM, including 1 to 2 µM (e.g., 1.2 µM).

The template switch oligonucleotide may include one or more nucleotides (or analogs thereof) that are modified or otherwise non-naturally occurring. For example, the template switch oligonucleotide may include one or more nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nucleotides, or any other feature that provides a desired functionality to the template switch oligonucleotide.

In certain aspects, the template switch oligonucleotide includes a 3' hybridization domain and/or a 5' adapter sequence. The 3' hybridization domain may vary in length, and in some instances ranges from 2 to 10 nts in length, such as 3 to 7 nts in length . . . . According to one embodiment, the polymerase (e.g., a reverse transcriptase such as MMLV RT) combined into the reaction mixture has terminal transferase activity such that a homonucleotide stretch (e.g., a homo-trinucleotide, such as C-C-C) may be added to the 3' end of a nascent strand, and the 3' hybridization domain of the template switch oligonucleotide includes a homonucleotide stretch (e.g., a homo-trinucleotide, such as G-G-G) complementary to that of the 3' end of the nascent strand. In other aspects, when the polymerase having terminal transferase activity adds a nucleotide stretch to the 3' end of the nascent strand (e.g., a trinucleotide stretch), the 3' hybridization domain of the template switch oligonucleotide includes a hetero-trinucleotide comprises a nucleotide comprising cytosine and a nucleotide comprising guanine (e.g., an r(C/G)$_3$ oligonucleotide), which hetero-trinucleotide stretch of the template switch oligonucleotide is complementary to the 3' end of the nascent strand. Examples of 3' hybridization domains and template switch oligonucleotides are further described in U.S. Pat. No. 5,962,272, the disclosure of which is herein incorporated by reference.

According to one embodiment, the template switch oligonucleotide includes a modification that prevents the polymerase from switching from the template switch oligonucleotide to a different template nucleic acid after synthesizing the compliment of the 5' end of the template switch oligonucleotide (e.g., a 5' adapter sequence of the template switch oligonucleotide). Useful modifications include, but are not limited to, an abasic lesion (e.g., a tetrahydrofuran derivative), a nucleotide adduct, an iso-nucleotide base (e.g., isocytosine, isoguanine, and/or the like), and any combination thereof.

When the template switch oligonucleotide includes a 5' adapter sequence (e.g., a defined nucleotide sequence 5' of the 3' hybridization domain of the template switch oligonucleotide), the 5' adapter sequence may serve as a template for generating a product nucleic acid having a primer binding site (complementary to the 5' adapter sequence) at its 3' end useful, e.g., for performing second strand synthesis and/or PCR amplification using the newly-synthesized product nucleic acid as a template. Accordingly, the methods may further include synthesizing the product nucleic acid all the way to the 5' end of a template switch oligonucleotide having a 5' adapter sequence, followed by contacting (e.g., hybridizing) the 3' end of the product nucleic acid (complementary to the 5' adapter sequence of the template switch oligonucleotide) with a second strand primer configured to bind thereto under hybridization conditions.

The term "complementary" as used herein refers to a nucleotide sequence that base-pairs by non-covalent bonds to all or a region of a target nucleic acid (e.g., a region of the product nucleic acid). In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to every nucleotide in the target nucleic acid in all the corresponding positions. For example, a primer may be perfectly (i.e., 100%) complementary to the target nucleic acid, or the primer and the target nucleic acid may share some degree of complementarity which is less than perfect (e.g., 70%, 75%, 85%, 90%, 95%, 99%). The percent identity of two nucleotide sequences can be determined by aligning the sequences for optimal comparison purposes (e.g., gaps can be introduced in the sequence of a first sequence for optimal alignment). The nucleotides at corresponding positions are then compared, and the percent identity between the two sequences is a function of the number of identical positions shared by the sequences (i.e., % identity=# of identical positions/total # of positions×100). When a position in one sequence is occupied by the same nucleotide as the corresponding position in the other sequence, then the molecules are identical at that position. A non-limiting example of such a mathematical algorithm is described in Karlin et al., Proc. Natl. Acad. Sci. USA 90:5873-5877 (1993). Such an algorithm is incorporated into the NBLAST and XBLAST programs (version 2.0) as described in Altschul et al., Nucleic Acids Res. 25:389-3402 (1997). When utilizing BLAST and Gapped BLAST programs, the default parameters of the respective programs (e.g., NBLAST) can be used. In one aspect, parameters for sequence comparison can be set at score=100, wordlength=12, or can be varied (e.g., wordlength=5 or wordlength=20).

As used herein, the term "hybridization conditions" means conditions in which a primer specifically hybridizes to a region of the target nucleic acid (e.g., the product nucleic acid). Whether a primer specifically hybridizes to a target nucleic acid is determined by such factors as the degree of complementarity between the polymer and the target nucleic acid and the temperature at which the hybridization occurs, which may be informed by the melting temperature ($T_M$) of the primer. The melting temperature refers to the temperature at which half of the primer-target nucleic acid duplexes remain hybridized and half of the duplexes dissociate into single strands. The $T_m$ of a duplex may be experimentally determined or predicted using the following formula $T_m=81.5+16.6(\log_{10}[Na^+])+0.41$ (fraction G+C)−(60/N), where N is the chain length and $[Na^+]$ is less than 1 M. See Sambrook and Russell (2001; Molecular Cloning: A Laboratory Manual, $3^{rd}$ ed., Cold Spring Harbor Press, Cold Spring Harbor N.Y., Ch. 10). Other more advanced models that depend on various parameters may also be used to predict $T_m$ of primer/target duplexes depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993).

As set forth above, the methods may include synthesizing the product nucleic acid and hybridizing the 3' end of the product nucleic acid (complementary to the 5' adapter sequence) to a second strand primer. In such embodiments, the methods may further include subjecting the reaction mixture to nucleic acid polymerization conditions (e.g., as described elsewhere herein) to generate a second strand DNA complementary to the product nucleic acid.

As described above, the subject methods include combining dNTPs into the reaction mixture. In certain aspects, each of the four naturally-occurring dNTPs (dATP, dGTP, dCTP and dTTP) are added to the reaction mixture. For example, dATP, dGTP, dCTP and dTTP may be added to the reaction mixture such that the final concentration of each dNTP is from 0.01 to 100 mM, such as from 0.1 to 10 mM, including 0.5 to 5 mM (e.g., 1 mM). According to one embodiment, at least one type of nucleotide added to the reaction mixture is a non-naturally occurring nucleotide, e.g., a modified nucleotide having a binding or other moiety (e.g., a fluorescent moiety) attached thereto, a nucleotide analog, or any other type of non-naturally occurring nucleotide that finds use in the subject methods or a downstream application of interest.

The addition of a primer to the reaction mixture is not necessary when the template DNA provides a suitable substrate for initiation of first-strand synthesis. For example, when the template DNA is a double-stranded DNA having an overhang at one or both of its ends, the "non-overhanging" strand of the dsDNA can prime a first-strand synthesis reaction in which the overhanging strand serves as the template. In this manner, the polymerase may be used to "fill in" the overhang, switch to the template switch oligonucleotide, and complete the first strand synthesis using the template switch oligonucleotide as an acceptor template to produce the product nucleic acid (where a terminal transferase reaction by the polymerase optionally precedes the template switch as described elsewhere herein). Accordingly, the addition of a primer is obviated, e.g., when the template DNA is double stranded and includes an overhang at one or both of its ends.

In certain circumstances, however, it may be desirable to add a primer to the reaction mixture to prime the first-strand synthesis reaction. For example, if the template DNA is single-stranded, or if the template DNA is a double-stranded DNA having blunt ends, a primer may be useful for purposes of initiating first-strand synthesis. In addition, use of a primer can give a practitioner of the subject methods more control over which DNA(s) in a DNA sample will serve as the template DNA(s) for production of the product nucleic acid, e.g., where it is desirable to produce product nucleic acids corresponding to a template DNA of interest having a known sequence (and not produce product nucleic acids from other DNA species in the sample).

Accordingly, in certain aspects, the subject methods further include contacting the template DNA with a first primer. The contacting is performed under conditions sufficient for the primer to hybridize to the template DNA, which conditions are described elsewhere herein. According to one embodiment, the entire sequence of the primer is arbitrary, e.g., the primer may be a random hexamer or any other random primer of suitable length (or mixtures thereof). In other aspects, the primer has a defined sequence, e.g., the primer sequence may be designed by one practicing the subject methods to specifically hybridize to a known complementary sequence in a template DNA of interest.

According to one embodiment, the primer includes two or more domains. For example, the primer may include a first (e.g., 3') domain that hybridizes to the template DNA and a second (e.g., 5') domain that does not hybridize to the template DNA. The sequence of the first and second domains may be independently defined or arbitrary. In certain aspects, the first domain has a defined sequence and the sequence of the second domain is defined or arbitrary. In other aspects, the first domain has an arbitrary sequence (e.g., a random sequence, such as a random hexamer sequence) and the sequence of the second domain is defined or arbitrary. According to one embodiment, the second domain includes a nucleotide sequence that is identical to a nucleotide sequence present in the template switch oligonucleotide. This embodiment finds use, e.g., when having identical sequences (e.g., identical "adapter" sequences) flanking a DNA facilitates a downstream application of interest (e.g., cloning, sequencing, etc.). Alternatively, or additionally, the second domain may include a nucleotide sequence that is not present in the template switch oligonucleotide. For example, the second domain may constitute a first adapter sequence and a domain of the template switch oligonucleotide may constitute a second adapter sequence, where the first and second adapter sequences are different (see, e.g., adapter sequences A/A' and B/B' of the embodiment shown in FIG. 1). This embodiment finds use, e.g., where one wishes to produce DNAs with one end having an adapter sequence and the second end having a different adapter sequence. Having ends with different adapter sequences is useful, e.g., for preparing libraries of genomic DNA for subsequent cluster generation and DNA sequencing using an Illumina®-based sequencing platform or any other suitable sequencing platform, as desired.

Once the product nucleic acid is produced, the methods may include inputting the product nucleic acid directly into a downstream application of interest (e.g., cloning, sequencing, etc.). In other aspects, the methods may include using the product nucleic acid as a template for second-strand synthesis and/or PCR amplification. According to one embodiment, the methods of the present disclosure further include subjecting the product nucleic acid to nucleic acid amplification conditions. Such conditions may include the addition of forward and reverse primers configured to amplify all or a desired portion of the product nucleic acid, dNTPs, and a polymerase suitable for effecting the amplification (e.g., a thermostable polymerase). An initial step in carrying out the amplification may include denaturing the product nucleic acid to dissociate the template DNA and template switch oligonucleotide from the product nucleic acid, thereby making the product nucleic acid available for primer binding.

A method according to one embodiment of the present disclosure is schematically shown in FIG. 1. As shown, template DNA 102, polymerase 104, template switch oligonucleotide 106, and dNTPs (not shown) are combined into reaction mixture 100 under conditions sufficient to produce the product nucleic acid. Although optional, the embodiment shown in FIG. 1 employs a first primer, primer 108, which is extended by the polymerase for first strand synthesis. Primer 108 includes first (3') domain 110 that hybridizes to the template DNA and second (5') domain 112 that does not hybridize to the template DNA. The nucleotide sequence of first domain 110 may be arbitrary (e.g., a random sequence, such as a random hexamer sequence) or the sequence of the first domain may be defined (e.g., a sequence specifically selected to hybridize to a particular region of a particular template DNA of interest). In this example, first domain 110 of primer 108 is complementary to sequence 114 within template DNA 102.

Upon hybridization of primer 108 to template DNA 102, first strand synthesis proceeds when polymerase 104 extends primer 108 along template DNA 102. In this example, the polymerase has terminal transferase activity, such that when the extension reaction reaches the 5' end of the template DNA, the polymerase adds a homonucleotide stretch (e.g., a homotrinucleotide shown here as XXX) to the extension product. According to this embodiment, template switch oligonucleotide has a 3' hybridization domain that includes a homotrinucleotide (also shown as XXX) complementary to the homonucleotide stretch at the 3' end of the extension product. This complementarity promotes hybridization of the 3' hybridization domain of the template switch oligonucleotide to the 3' end of the extension product. This hybridization brings the acceptor template (or "adapter sequence" (B')) region of the template switch oligonucleotide (located 5' of the 3' hybridization domain) within sufficient proximity of the polymerase such that the polymerase can template switch to the acceptor template region and continue the extension reaction to the 5' terminal nucleotide of the template switch oligonucleotide, thereby producing the product nucleic acid that includes the template DNA and the template switch oligonucleotide each hybridized to adjacent regions of the single product nucleic acid.

In this example, the method further includes a second strand synthesis step, where a primer having a sequence (B') complementary to a 3' region (B) of the product nucleic acid hybridizes to the 3' region of the product nucleic acid and is extended by a polymerase—using the product nucleic acid as a template—to the 5' end of the product nucleic acid. The result of this second strand synthesis step is a double-stranded DNA that includes the product nucleic acid and its complementary strand.

According to the embodiment shown in FIG. 1, the double-stranded DNA resulting from second-strand synthesis includes adapter sequences (shown in FIG. 1 as A/A' and B/B') which may be useful in a variety of downstream applications of interest including, but not limited to, PCR amplification, cloning, sequencing, and any other application in which having defined sequences at the ends of DNA molecules is advantageous.

The following section provides further description of different embodiments of the invention. According to one embodiment, a double-stranded template DNA is combined with a template switch oligonucleotide having a defined sequence, a polymerase, and dNTPs. A 3' end of the dsDNA template is extended by the polymerase using as templates the dsDNA template and then the template switch oligonucleotide having the defined sequence. The resulting product nucleic acid may be subsequently amplified using primers complementary to all or a portion of the defined sequence.

According to another embodiment, a single- or double-stranded template DNA is combined with a first primer having a defined 5' sequence, a template switch oligonucleotide having a 5' sequence that is the same as the 5' defined sequence of the first primer, a polymerase, and dNTPs. The first primer having the defined 5' sequence hybridizes to the template DNA (which may be denatured prior to hybridization) and its 3' end is extended by the polymerase using as templates the template DNA and then the template switch oligonucleotide. The resulting product nucleic acid will have the defined sequence at its 5' and 3' ends. This nucleic acid may then be amplified using primers complementary to all or a portion of the defined sequence. In certain aspects, this nucleic acid may be amplified both from random priming and template switching addition.

In a further embodiment, precursor double-stranded DNAs having blunt ends are pre-treated with an enzyme that generates template DNAs having 3' overhangs. For example, the precursor double-stranded DNAs may be treated with a terminal transferase enzyme and/or a restriction enzyme to generate template DNAs having 3' overhangs. Next, a polymerase (e.g., a reverse transcriptase) is used to extend the non-overhanging strand of the template DNA using the overhanging strand as the template. When the polymerase reaches the end of the overhanging strand, terminal transferase activity of the polymerase adds a stretch of nucleotides by non-templated nucleotide addition (e.g., addition of a homo-nucleotide stretch (e.g., a homo-trinucleotide stretch such as CCC), a hetero-trinucleotide stretch, or the like). According to this embodiment, the template switch oligonucleotide has a 3' end complementary to the stretch added by the polymerase via non-templated nucleotide addition. Upon hybridization of the template switch oligonucleotide to the stretch added by non-templated nucleotide addition, the polymerase is able to template switch to the template switch oligonucleotide and continue the extension reaction by synthesizing the complement of the 5' region of the template switch oligonucleotide. When the method employs a restriction enzyme to generate the 3' overhangs, the method could be designed such that the extension reaction destroys the restriction site, allowing the fragmentation and tagging functionalities to be provided in a single tube that includes one or more 3' overhang-generating restriction enzymes, a polymerase, a template switch oligonucleotide, and any other desirable reaction components, in a suitable buffer.

The subject methods may be employed to generate libraries of nucleic acids in which the nucleic acids have adapter sequences at their 5' and 3' ends. The nucleic acids may have the same adapter sequence at their 5' and 3' ends, or the adapter sequences at the 5' and 3' ends may be different. For certain applications, such as certain next generation sequencing approaches (e.g., genomic sequencing using Illumina®-based sequencing platforms), it is required that the input DNAs have different adapter sequences at the different ends of the DNA. Accordingly, any of the compatible embodiments described elsewhere herein could be performed with a mix of "A" and "B" acceptors, combined with suppression PCR to generate DNAs having an "A" adapter at one end and a "B" adapter at the other end. For example, the template DNA could be combined with "A" and "B" acceptors each having a suppression element, a suitable polymerase, and dNTPs to produce product nucleic acids having an "A" adapter at one end and a "B" adapter at the other end. Also provided is a variation of this embodiment where priming (e.g., random or non-random priming) of either single- or double-stranded DNA could be performed using a primer with an "A" sequence and suppression element in a reaction with a template switch oligonucleotide having a "B" acceptor and a suppression element. Here, the polymerase extends the "A" primer, then switches templates to the "B" acceptor, resulting in a product nucleic acid having an "A" adapter at its 5' end and a "B" adapter at its 3' end.

In any of the embodiments in which a product nucleic acid is generated having the same or different adapters at its ends, the template DNA may be a double-stranded template DNA generated from a precursor DNA in which the precursor DNA is treated with, e.g., a terminal transferase enzyme and/or a restriction enzyme, such that the double-stranded template DNA has 3' overhangs. A polymerase (e.g., a reverse transcriptase) may be used to extend the non-overhanging strand of the template DNA using the overhanging strand as the template. When the polymerase reaches the end of the overhanging strand, terminal transferase activity of the polymerase adds a stretch of nucleotides by non-templated nucleotide addition (e.g., addition of a homo-nucleotide stretch (e.g., a homo-trinucleotide stretch such as CCC), a hetero-trinucleotide stretch, or the like). According to this embodiment, a mixture of template switch oligonucleotides having 3' ends complementary to the stretch added by the polymerase via non-templated nucleotide addition and either an A adapter sequence or B adapter sequence is provided. Upon hybridization of the template switch oligonucleotide to the stretch added by non-templated nucleotide addition, the polymerase is able to template switch to the template switch oligonucleotide and continue the extension reaction by synthesizing the complement of the A adapter sequence or the B adapter sequence of the template switch oligonucleotide. When the 3' overhangs are generated via restriction enzyme digestion, the digestion could be performed using a mixture of restriction enzymes.

In certain aspects, the subject methods may further include combining a thermostable polymerase—in addition to the template switching polymerase—into the reaction mixture. Alternatively, the template switching polymerase may be a thermostable polymerase. Either of these embodiments find use, e.g., when it is desirable to achieve adaptor addition and amplification of the product nucleic acid in a single tube. Here again, the template DNAs may be double-stranded template DNAs having 3' overhangs complementary to the 3' end of an acceptor template switch oligonucleotide.

The subject methods also find use in constructing novel DNA molecules (in addition to the novel molecules described elsewhere herein having one or more adapter sequences at one or both of its ends), e.g., by gene shuffling. For example, the subject methods may be used to generate a nucleic acid having the sequence "AB" starting from a first DNA molecule having an "A" sequence and a second DNA molecule having a "B" sequence. According to one embodiment, a template DNA having an "A" sequence may be extended with the polymerase and then template switch onto an acceptor template switch nucleic acid having a "B" sequence, thereby generating a first product nucleic acid having a continuous "AB" sequence. In certain aspects, the acceptor template switch nucleic acid having a "B" sequence may be a vector, such that the method is a method of cloning the "A" sequence in a single step (e.g., without any separate ligation step(s)).

Compositions

Also provided by the present disclosure are compositions. The subject compositions may include, e.g., one or more of any of the reaction mixture components described above with respect to the subject methods. For example, the compositions may include one or more of a template deoxyribonucleic acid (DNA), a polymerase (e.g., a polymerase capable of template-switching, a thermostable polymerase, combinations thereof, or the like), a template switch oligonucleotide, dNTPs, a salt, a metal cofactor, one or more nuclease inhibitors (e.g., a DNase inhibitor), one or more enzyme-stabilizing components (e.g., DTT), an enzyme capable of generating dsDNAs having 3' overhangs from precursor dsDNAs (e.g., a restriction endonuclease, a terminal transferase, or a combination thereof), or any other desired reaction mixture component(s).

In certain aspects, the subject compositions include a template deoxyribonucleic acid (DNA) and a template switch oligonucleotide each hybridized to adjacent regions of a nucleic acid strand. The template DNA may be any template DNA of interest, e.g., a genomic DNA or fragment thereof, a cDNA or fragment thereof, and/or the like. Approaches for isolating DNA samples from a nucleic acid source of interest, as well as strategies for generating template DNAs from precursor DNAs, are described elsewhere herein.

The template switch oligonucleotide may have one or more domains/sequences useful, e.g., when practicing the subject methods or in any downstream application in which the nucleic acid strand finds use (e.g., PCR amplification, cloning, sequencing, and/or any other downstream application of interest). In certain aspects, the template switch oligonucleotide includes a 3' hybridization domain (e.g., a homonucleotide stretch (e.g., a homo-trinucleotide) or a heteronucleotide stretch (e.g., r(C/G)$_3$)) and a 5' adapter sequence (e.g., a defined nucleotide sequence 5' of the 3' hybridization domain of the template switch oligonucleotide).

The subject compositions may be present in any suitable environment. According to one embodiment, the composition is present in a reaction tube (e.g., a 0.2 mL tube, a 0.6 mL tube, a 1.5 mL tube, or the like) or a well. In certain aspects, the composition is present in two or more (e.g., a plurality of) reaction tubes or wells (e.g., a plate, such as a 96-well plate). The tubes and/or plates may be made of any suitable material, e.g., polypropylene, or the like. In certain aspects, the tubes and/or plates in which the composition is present provide for efficient heat transfer to the composition (e.g., when placed in a heat block, water bath, thermocycler, and/or the like), so that the temperature of the composition may be altered within a short period of time, e.g., as necessary for a particular enzymatic reaction to occur. According to certain embodiments, the composition is present in a thin-walled polypropylene tube, or a plate having thin-walled polypropylene wells. In certain embodiments it may be convenient for the reaction to take place on a solid surface or a bead, in such case, the template switch oligonucleotide or one or more of the primers may be attached to the solid support or bead by methods known in the art—such as biotin linkage or by covalent linkage) and reaction allowed to proceed on the support.

Other suitable environments for the subject compositions include, e.g., a microfluidic chip (e.g., a "lab-on-a-chip device"). The composition may be present in an instrument configured to bring the composition to a desired temperature, e.g., a temperature-controlled water bath, heat block, or the like. The instrument configured to bring the composition to a desired temperature may be configured to bring the composition to a series of different desired temperatures, each for a suitable period of time (e.g., the instrument may be a thermocycler).

Kits

Aspects of the present disclosure also include kits. The subject kits may include, e.g., one or more of any of the reaction mixture components described above with respect to the subject methods. For example, the kits may include one or more of a template deoxyribonucleic acid (DNA), a polymerase (e.g., a polymerase capable of template-switching, a thermostable polymerase, combinations thereof, or the like), a template switch oligonucleotide, dNTPs, a salt, a metal cofactor, one or more nuclease inhibitors (e.g., an RNase inhibitor and/or a DNase inhibitor), one or more additives for facilitating amplification/replication of GC rich sequences (e.g., GC-Melt™ reagent (Clontech Laboratories, Inc. (Mountain View, Calif.)), betaine, DMSO, ethylene glycol, 1,2-propanediol, or combinations thereof), one or more molecular crowding agents (e.g., polyethylene glycol, or the like), one or more enzyme-stabilizing components (e.g., DTT), an enzyme capable of generating dsDNAs having 3' overhangs from precursor dsDNAs (e.g., a restriction endonuclease, a terminal transferase, or a combination thereof), or any other desired kit component(s), such as containers and/or solid supports, e.g., tubes, beads, microfluidic chips, and the like.

According to one embodiment, the subject kits include a 3' overhang-generating enzyme, a polymerase having terminal transferase activity, and a template switch nucleic acid having a 3' end complementary to a nucleotide stretch produced by the polymerase via non-templated nucleotide addition. Any enzyme capable of generating a 3' overhang from a precursor double-stranded DNA may be included in the subject kits. For example, the enzyme may be a restriction endonuclease capable of producing a DNA (e.g., a template DNA employed when practicing the subject methods) having a 3' overhang at one or both ends of the template DNA. Restriction endonucleases and the types of overhangs generated thereby are well characterized and can be selected by one practicing the subject methods to produce a DNA having a desired type of overhang. In certain aspects, the 3' overhang-generating enzyme is a terminal transferase, where the terminal transferase is capable of non-templated extension of a 3' end of a dsDNA in the presence of one or more types of dNTPs to generate a desired 3' overhang.

When the subject kits include a template switch nucleic acid, the template switch nucleic acid may include one or more domains/sequences useful, e.g., when practicing the subject methods or in any downstream application of interest. In certain aspects, the template switch nucleic acid includes a defined sequence at a region 5' of the 3' overhang. This defined region may be an adapter sequence useful for, e.g., a second-strand synthesis reaction, PCR amplification, cloning, sequencing, and/or the like. When such a defined sequence at a region 5' of the 3' overhang is present in the template switch nucleic acid, the subject kits may include a primer having the defined sequence (e.g., for amplification of a nucleic acid species having a sequence complementary to the defined sequence).

In certain aspects, the template switch nucleic acid includes a cloning vector element. The cloning vector element may be a selectable marker (e.g., a genetic element that confers on a host organism resistance to a selection agent), a reporter gene (e.g., a gene that encodes a fluorescent protein (e.g., GFP, RFP, or the like), beta-galactosidase, beta-glucuronidase, chloramphenicol acetyltransferase (CAT), or any other useful reporter gene), a promoter (e.g., a T7, T3, or other promoter), an origin of replication (e.g., oriC), a multiple cloning site, or any combination of cloning vector elements.

In certain embodiments, the kits include reagents for isolating a nucleic acid sample from a nucleic acid source. The reagents may be suitable for isolating nucleic acid samples from a variety of sources including single cells, cultured cells, tissues, organs, or organisms. The subject kits may include reagents for isolating a nucleic acid sample from a fixed cell, tissue or organ, e.g., formalin-fixed, paraffin-embedded (FFPE) tissue. Such kits may include one or more deparaffinization agents, one or more agents suitable to de-crosslink nucleic acids, and/or the like.

Components of the subject kits may be present in separate containers, or multiple components may be present in a single container. For example, a 3' overhang-generating enzyme and a template switch nucleic acid may be provided in separate containers, or may be provided in a single container. In certain embodiments, one or more kit components is provided in a lyophilized form such that the components are ready to use and may be conveniently stored at room temperature.

In addition to the above-mentioned components, a subject kit may further include instructions for using the components of the kit, e.g., to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The subject methods find use in a variety of applications that benefit from, e.g., use of nucleic acids that include a region of known sequence at one or both ends of the nucleic acids. Such applications exist in the areas of basic research and diagnostics (e.g., clinical diagnostics) and include—but are not limited to—nucleic acid cloning, amplification, detection, library generation/amplification, array hybridization, whole-genome amplification, whole-genome sequencing, and any other application in a which a product nucleic generated according to the subject methods find use. A key aspect of the subject methods is that—utilizing a template DNA—a nucleic acid species is generated having a region(s) of known sequence at one or both of its ends in a single step, e.g., without the added steps associated with traditional ligation-based approaches for generating hybrid nucleic acid molecules. Accordingly, the subject methods are more efficient, cost-effective, and provide more flexibility than the traditional approaches.

The following examples are offered by way of illustration and not by way of limitation.

EXPERIMENTAL

I. Generation of a Single Product Nucleic Acid from Two Separate DNAs

In this experiment, a 20 base pair DNA labeled at its 5' end with 6-FAM was hybridized to a 40 base pair template DNA complementary to the 20 base pair DNA at its 3' end. The hybridized 20 base pair DNA was extended using wild-type MMLV reverse transcriptase or SMARTScribe™ reduced RNAseH reverse transcriptase (Clontech Laboratories, Inc. (Mountain View, Calif.)) in the presence or absence of the SMARTer™ IIA template switch oligonucleotide (Clontech Laboratories, Inc. (Mountain View, Calif.)). The products of the reaction were resolved on a TBE-UREA acrylamide gel, and an additional band of greater length was observed when extended by either polymerase and only in the presence of the template switch oligonucleotide.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method comprising:
   combining:
      a template deoxyribonucleic acid (DNA);
      a retroviral reverse transcriptase;
      a template switch oligonucleotide;
      a first DNA primer comprising a 3' domain that hybridizes to the template DNA; and
      dNTPs;
   into a reaction mixture under conditions sufficient to produce a product nucleic acid, wherein the product nucleic acid comprises the template DNA and the template switch oligonucleotide each hybridized to adjacent regions of a single hybrid nucleic acid comprising a region polymerized from the dNTPs by the retroviral reverse transcriptase, wherein the region polymerized from the dNTPs comprises a domain that is complementary to and hybridized to the 5' end of the template DNA.

2. The method according to claim 1, wherein the template switch oligonucleotide comprises a 3' hybridization domain and a 5' adapter sequence.

3. The method according to claim 2, wherein the 3' hybridization domain comprises a homo-trinucleotide.

4. The method according to claim 2, wherein the 3' hybridization domain comprises a hetero-trinucleotide.

5. The method according to claim 4, wherein the hetero-trinucleotide comprises a nucleotide comprising cytosine and a nucleotide comprising guanine.

6. The method according to claim 1, wherein the template switch oligonucleotide comprises a modification that prevents the retroviral reverse transcriptase from switching from the template switch oligonucleotide to a different template nucleic acid after synthesizing the complement of the template switch oligonucleotide.

7. The method according to claim 1, wherein the method further comprises contacting a 3' region of the single hybrid nucleic acid with a second strand primer configured to bind thereto under hybridization conditions.

8. The method according to claim 1, wherein the method further comprises subjecting the single hybrid nucleic acid to nucleic acid amplification conditions.

9. The method according to claim 1, wherein the template DNA is single stranded.

10. The method according to claim 1, wherein the template DNA is double-stranded.

11. The method according to claim 10, wherein the double-stranded template DNA comprises a 3' overhang.

12. The method according to claim 11, wherein the method further comprises producing the template DNA from a precursor double-stranded DNA.

13. The method according to claim 12, wherein the method comprises contacting the precursor double-stranded DNA with a terminal transferase under conditions sufficient to produce the template DNA.

14. The method according to claim 12, wherein the method comprises contacting the precursor double-stranded DNA with a restriction enzyme to produce the template DNA.

15. The method according to claim 2, wherein the first DNA primer comprises a 5' adapter sequence.

* * * * *